(12) United States Patent
Orsenigo et al.

(10) Patent No.: US 8,216,960 B2
(45) Date of Patent: Jul. 10, 2012

(54) CATALYSTS FOR FIXED BED OXYCHLORINATION OF ETHYLENE TO 1.2-DICHLOROETHANE

(75) Inventors: Carlo Orsenigo, Milan (IT); Francesco Casagrande, Novara (IT); Marco Civati, Invorio (IT)

(73) Assignee: Sued-Chemie Catalysts Italia S.R.L., Novara (IT)

( * ) Notice: Subject to any disclaimer, the term of this patent is extended or adjusted under 35 U.S.C. 154(b) by 0 days.

(21) Appl. No.: 12/641,624

(22) Filed: Dec. 18, 2009

(65) Prior Publication Data
US 2010/0160697 A1    Jun. 24, 2010

(30) Foreign Application Priority Data
Dec. 23, 2008   (EP) .................................. 08172829

(51) Int. Cl.
*B01J 23/04* (2006.01)
(52) U.S. Cl. ......... 502/225; 502/345; 502/242; 570/203
(58) Field of Classification Search .................. None
See application file for complete search history.

(56) References Cited

U.S. PATENT DOCUMENTS

| | | | | |
|---|---|---|---|---|
| 4,414,136 A | * | 11/1983 | Convers | 502/225 |
| 4,740,644 A | | 4/1988 | Eichhorn et al. | |
| 5,166,120 A | * | 11/1992 | Deller et al. | 502/225 |
| H1800 H | | 8/1999 | Salinas, III et al. | |
| 6,452,059 B1 | * | 9/2002 | Casagrande et al. | 570/245 |
| 6,759,365 B2 | * | 7/2004 | Cavalli et al. | 502/346 |
| 6,872,684 B2 | * | 3/2005 | Casagrande et al. | 502/225 |
| 2005/0020864 A1 | * | 1/2005 | Kuhrs et al. | 570/203 |
| 2006/0129008 A1 | * | 6/2006 | Casagrande et al. | 570/234 |
| 2006/0270879 A1 | | 11/2006 | Kuhrs et al. | |

FOREIGN PATENT DOCUMENTS

| | | |
|---|---|---|
| EP | 1 053 789 A1 | 11/2000 |
| EP | 1 645 332 A1 | 4/2006 |
| WO | WO 96/40431 | 12/1996 |
| WO | WO 03/066214 A2 | 8/2003 |

* cited by examiner

*Primary Examiner* — Melvin C Mayes
*Assistant Examiner* — Colette Nguyen
(74) *Attorney, Agent, or Firm* — Scully, Scott, Murphy & Presser, P.C.

(57) ABSTRACT

Catalyst for the fixed bed oxychlorination of ethylene to 1,2-dichloroethane in form of hollow cylindrical granules having total pore volume from 0.4 to 0.55 ml/g prevailingly formed of micro and mesopores having diameter between 7 and 50 nm, wherein the mesopores constitute the major component, and the macropores having diameter of more than 50 nm up to 10,000 nm being present by 15-35%.

13 Claims, No Drawings

CATALYSTS FOR FIXED BED OXYCHLORINATION OF ETHYLENE TO 1.2-DICHLOROETHANE

The present invention relates to catalysts usable in fixed-bed oxychlorination of ethylene to 1,2-dichloroethane (DCE) in form of granules having definite hollow cylindrical shape and total pore volume comprised in a specific range wherein the mesopores with diameter from 7 to 50 nm are the major component, and to the hollow carriers used for said catalysts.

BACKGROUND OF THE INVENTION

The oxychlorination of ethylene to DCE is carried out, as it is known, either in fluid bed or in fixed bed. In the first case, more uniform distribution of the temperatures in the reactor is obtained, in the other case, the management of reaction parameters is easier but, due to the low exchange coefficient among the catalyst granules and between the granules and the reaction gas, localized hot spot temperatures can occur having detrimental effects on the selectivity and useful life of the catalyst.

Hollow cylindrical granules are normally used which, thanks to S/V ratio (geometric surface to volume ratio) higher than that of the spheres and solid cylinders allow to obtain more efficient heat exchange and lower pressure drop through the catalytic bed, and consequently better temperature control along the bed and increased productivity of industrial reactors.

In spite of the above advantages, a hollow cylindrical granule has to be designed carefully since, otherwise several disadvantages become evident.

For example, if the ratio of the external to internal diameter (De/Di) of the hollow cylinder is greater than a certain value, the granules become too fragile and the bulk density of the catalyst decreases resulting in a decreased conversion per unit volume of the catalytic bed due to the lower presence of total content of the active catalyst phase.

A too high increase of De or the length of the cylinders maintaining constant the De/Di ratio can cause an inhomogeneous loading of the catalyst inside the tubes of the reactor and possible breakage of the granules with consequent increase of the pressure drop.

A catalyst in form of cylinders having De from 4 to 7 mm, Di from 2.0 to 2.8 nm, height from 6.1 to 6.9 mm is described in EP 1 053 789 A1.

This catalyst is reported to be advantageous with respect to the catalysts in form of hollow cylinders having length shorter than the external diameter described in U.S. Pat. No. 4,740,644 and the catalyst cylinders having longer length than the external diameter described in U.S. Pat. No. 5,166,120.

The catalysts of the latter cited US patent are also characterized by a total pore volume of at least 0.6 to 1.0 ml/g, wherein no pores smaller than 4 nm are present and at least 80% of the total pore volume is formed of mesopores with a diameter of 8 to 20 nm, the remainder being pores with diameter of more than 20 nm and up to 200 nm.

The catalysts of U.S. Pat. No. 5,166,120, according to the consideration made in EP 1 053 789, has the disadvantage of a too high bed void fraction which implies a lower amount of catalytic material present in the bed and consequently a lower specific productivity to DCE (g DCE/g catalyst.h) combined with high pressure drop due to breakage of the catalyst granules during the loading step. The activity of the catalysts is higher than that of catalysts the pore volume of which is mainly formed of pores with diameter of less than 8 nm.

Commercial hollow cylindrical catalysts are known having total pore volume of at most 0.40 ml/g wherein the micro and mesopores are the major component. The productivity of these catalysts is rather low.

Objects

It is an object of the present invention to provide catalysts for the fixed bed oxychlorination of ethylene to DCE in form of hollow cylindrical granules having rather high total volume comprising copper chloride and at least one chloride of the metals selected from the alkali metals, the alkaline earth metals and the rare earth metals supported on gamma alumina hollow cylindrical granules, endowed with high performance in terms of selectivity and conversion combined with specific productivity to DCE (g DCE/g catalyst.h), higher than that of catalysts having the same geometrical parameters (shape and size) and composition.

This and other objects are accomplished by the catalysts of the present invention.

Other objects will be apparent from the following description of the invention.

SUMMARY OF THE INVENTION

The catalysts of the present invention, which are in form of hollow granules having definite geometrical configuration and comprise copper chlorides, preferably also potassium chloride and optionally at least one or more chlorides of the metals selected from the group of the alkali metals, alkaline earth metals and rare earth metals supported on alumina hollow cylindrical granules, are characterized by a total pore volume of 0.4 to 0.55, preferably 0.40-0.48 ml/g prevailingly formed of micro and mesopores wherein the mesopores with diameter from 7 to 50 nm constitute the major component, the remaining being formed of macropores with diameter of more than 50 nm and up to 10,000 nm, which constitute the 15-35%, preferably 20-35% of the total volume. The average pore diameter is from 10 to 20 nm. By total pore volume is meant the volume which is the difference between the reciprocals of the particle density (PD) and the real density (RD) ($^1$/PD−$^1$/RD).

DETAILED DESCRIPTION OF THE INVENTION

The alumina support is prepared by compression shaping of boehmite powder having $d_{50}$ of about 60-65 µm, $d_{90}$ of about 160-165 µm and average diameter of 70-80 µm (laser determination).

An example of usable boehmite is the commercial boehmite V 700 VERSAL manufactured by UOP (USA).

This boehmite has particle diameter distribution (laser determination) as follows:

| diameter less than: | volume % |
|---|---|
| 40 µm | 34.2 |
| 63 µm | 51.0 |
| 100 µm | 70.4 |
| 250 µm | 99.6 |
| 100 µm | 100 |

The size distribution (wt %) determined by ponderal sieve screening is: <63 µm 52.1%, 63-100 µm=24.8%, 100-250 µm=22.0%, >250 µm=1.1%.

The usable boehmites are obtained according to known methods by precipitation of Al(OH)$_3$ from aqueous solution of NaAlO₂ under controlled pH conditions and thoroughly washing the filtrate to remove as much as possible sodium ions.

The compression-shaped hollow cylindrical granules obtained from the boehmite V 700 VERSAL, calcined at 600° C. and 700° C., have the characteristics reported in Table 1, wherein the characteristics of boehmites Pural SCC 150 and PURAL SB1 commercialized by SASOL—Germany are also reported.

Granules having trilobed cross-section with the lobes provided with through bores parallel to the axis of the granules are also conveniently used.

Representative properties of the catalyst granules of the invention are reported in Table 2, while in Table 3 the results are reported of the catalysis tests obtained with the catalysts of the examples.

The oxychlorination of ethylene to DCE using the catalysts granules of the invention is carried out in fixed bed according

TABLE 1

| Alumina shaped support - Morphological properties | | | | |
|---|---|---|---|---|
| Shape | | Hollow Cyl. | Trilob. Cyl.[1] | Hollow Cyl. |
| Boehmite | | Versal V 700 | Versal V 700 | Pural SCC 150 |
| Lubricant | | Al-tristearate | Al-tristearate | Al-tristearate |
| Calcination | ° C. | 600 | 700 | 700 |
| Surface Area | m²/g | 209 | 164 | 208 |
| Particle Density | g/ml | 1.00 | 1.11 | 1.23 |
| Real Density | g/ml | 3.27 | 3.35 | 3.31 |
| Total Pore Volume[2] | nm | 0.694 | 0.602 | 0.511 |
| Average Pore Diameter[3] | | 13.3 | 14.7 | 9.8 |
| N₂ Ad. Des. (BET) | | | | |
| m.P.S. | nm | 9 | 10 | 5.5 |
| % Pores (D < 7 nm) on tot. P.V. | | 26 | 15 | 63 |
| % Meso Pore (8 < D < 20 nm) on tot. P.V. | | 38 | 52 | 8 |
| % Meso Pore (8 < D < 50 nm) on tot. P.V. | | 38 | 57 | 10 |
| % Pore Vol. (D < 7 nm) on Meso P.V. (D < 50 nm) | | 33 | 18 | 79 |
| Hg Porosimetry | | | | |
| Macro Pore Vol. (50 < D < 10.000 nm) | ml/g | 0.150 | 0.101 | 0.100 |
| % Macro Pore Vol. on tot. P.V. | | 22 | 17 | 20 |
| Weight 100 tablets | g | 6.36 | 6.70 | 8.25 |
| Height | mm | 4.70 | 4.35 | 4.90 |
| External Diameter | mm | 4.79 | 5.8[4] | 4.65 |
| Axial Crush Res. | Kg/tabl. | 73 ± 12 | 80 ± 11 | 86 ± 18 |
| Radial Crush Res. | Kg/tabl. | 2.01 ± 0.35 | 2.36 ± 0.31 | 1.9 ± 0.4 |

[1]Trilobed Cyl. = granules having circular-cross section and lobes with through bores parallel to the granule axis.
[2]Total Pore Volume = 1/(Particle Density) − (Real Density).
[3]Average Pore Diameter = 4 TV/SA (TV = Total Vol.; SA = Surface Area).
[4]Diameter of the circumscribed circonference.

The total pore volume of the alumina granules ranges from 0.55 to 0.75 ml/g and is prevailingly formed of mesopores (pores having diameter from 7 to 50 nm) and micropores (pores having diameter of less than 7 nm), wherein the micropores are the minor component (15-45% of the volume).

The obtained shaped granules (previous calcination at temperature from about 600° to 800° C. to convert boehmite into gamma alumina) are impregnated with an aqueous solution of the metal chlorides-catalyst components. The impregnation is preferably carried out using a volume of solution slightly higher than the pore volume of the alumina granules (wet impregnation).

The amount of the chlorides present in the catalyst expressed as metal is 3-12 wt % Cu, 1-4 wt % alkali metal, 0.05-2 wt % alkaline earth metal, 0.1-3 wt % rare earth metal.

Preferably the amount of Cu is from 4 to 10 wt %, and the alkali metal is potassium and/or cesium used in amount of 0.5 to 3 wt %, the alkaline earth metal is magnesium in amount of 0.05 to 2 wt % and the rare earth metal is cerium in amount of 0.5 to 3 wt %.

Preferred granules are in form of cylinders having at least one through bore parallel to the axis of the granule. The De diameter is from 4 to 6 mm, the Di diameter of 1 to 3 mm and the height of 4 to 7 mm.

to known methods using air or oxygen as oxidizer, at temperatures from 200° C. to 300° C., using overall feed molar ratios $C_2H_4/HCl/O_2$ of 1:1.99:0.51 when using air and of 1:0.71:0.18 when using oxygen.

Preferably, the molar ratios $HCl/C_2H_4$, $O_2/C_2H_4$ and $HCl/O_2$ are, respectively, 0.15 to 0.50, 0.04 to 0.1 and 3.20 to 5.8 when using oxygen and the process is carried out in three reactors in series, wherein the third reactor is loaded with a fixed bed formed or comprising the catalyst granules according to the invention.

Measurements

The macropore volume (volume of pores having diameter higher than 50 nm and up to 10,000 nm) is measured by Hg-porosimetry: the micro and the meso pore volume by BET nitrogen adsorption–desorption (meso pore volume=the volume of pores having 2 to 50 nm diameter).

The bulk density (called also apparent packing density) is measured according to ASTM method D 4164-82.

The following examples are given to illustrate but not to limit the scope of the invention.

EXAMPLE 1

350 g of alumina hollow cylinders with De=5 mm, Di=2.5 mm and height=5 mm obtained by calcination at 600° C. of cylinders prepared by compression-shaping of a powder of boehmite Versal V 700 mixed with 4 wt % of aluminum tristearate, having S.A. (BET) of 209 m$^2$/g, total pore volume of 0.69 ml/g, are impregnated in rotating jar of 5 l at room temperature up to 50° C., with 200 ml of an aqueous solution containing $CuCl_2*2H_2O$=97.0 g
KCl=6.9 g
$MgCl_2*6H_2O$=1.8 g
HCl 37 wt %=7.0 ml
Remaining=demineralized water up to 230 ml.

The impregnated granules were dried in an oven with the following cycle=1 h at 60° C., 2 hs at 80° C., 3 hs at 100° C. and 16 hs at 150° C.

The characteristics of the catalyst granules are reported in Table 2 wherein the characteristics of the catalyst granules of Example 2 and of comparative Example 1 and 2 are also reported.

The results of the pilot plant catalysis tests are reported in Table 3.

EXAMPLE 2

300 g of alumina granules having three-lobed circular cross section wherein each lobe is provided with a trough bore parallel to the axis of the granule, and the diameter of the circumscribed circonference being 5.8 mm and the height 4.30 mm, obtained by calcination at 700° C. of pellets prepared by compression-shaping of a powder of boehmite Versal V 700 to mixed with 4 wt % of aluminum tristearate, and S.A. (BET) of 164 m$^2$/g, total pore volume of 0.60 ml/g, are impregnated with an aqueous solution containing:

| | |
|---|---|
| $CuCl_2 * 2H_2O$ | 82.1 g |
| KCl | 5.9 g |
| HCl 37 wt % | 6.0 ml |

Remaining demineralized water.

The impregnated granules are dried as described in Example 1.

The characteristics of the catalyst granules are reported in Table 2.

COMPARISON EXAMPLE 1

400 g of alumina hollow cylinders having the same size and shape as the cylinders of Example 1, obtained by calcination at 700° C. of cylindrical granules prepared by compression-shaping of boehmite Pural SCC 150 mixed with 6 wt % of aluminum tristearate were impregnated in rotating jar of 5 l at r.t. with 150 ml of an aqueous solution containing:

$CuCl_2*2H_2O$=110.8 g

KCl=7.9 g $MgCl_2*6H_2O$=2.1 g

HCl 37 wt %=8.0 ml

Remaining=demineralized water up to 200 ml.

The impregnated granules are dried as described in Example 1.

The characteristics of the catalyst granules are reported in Table 2.

The results of the catalysis test carried out under the same conditions as of Example 1 are reported in Table 3.

COMPARISON EXAMPLE 2

A commercial catalysts having similar size and shape as the catalyst of Example 1 and similar composition (other properties are reported in Table 2) was used under the same catalysis test conditions as in Example 1.

The results of the test are reported in Table 3.

TABLE 2

| Catalyst | | Ex. 1 | Ex. 2 | Comp. Ex. 1 | Comp. Ex. 2 |
|---|---|---|---|---|---|
| Shape | | Hollow Cyl. | Trilobed Cyl. | Hollow Cyl. | Hollow Cyl. |
| Cu | wt % | 7.97 | 8.00 | 7.98 | 7.68 |
| K | wt % | 0.81 | 0.81 | 0.78 | 0.84 |
| Mg | wt % | 0.05 | — | 0.05 | 0.12 |
| Surface Area | m$^2$/g | 123 | 99 | 115 | 102 |
| Particle Density | g/ml | 1.29 | 1.37 | 1.55 | 1.78 |
| True Density | g/ml | 3.12 | 3.25 | 3.19 | 3.14 |
| Tot. Pore Vol. [1] | ml/g | 0.455 | 0.422 | 0.332 | 0.243 |
| Average Pore Diameter | nm | 14.8 | 17.1 | 11.5 | 9.5 |
| $N_2$ Ad-Des (BET) Porosimetry | | | | | |
| % Pore Vol. (D < 7 nm) on Tot. P.V. | | 20 | 18 | 46 | 66 |
| % Meso Pore Vol.(8 < D < 20 nm) on Tot. P.V. | | 41 | 51 | 17 | 7 |
| % Meso Pore Vol. (8 < D < 50 nm) on Tot. P.V. | | 48 | 58 | 20 | 9 |
| % Pore Vol. (D < 7 nm) on Meso P.V. (D < 50 nm) | | 29 | 23 | 69 | 88 |
| Hg Porosimetry | | | | | |
| Macro Pore Vol. (50 < 0 < 10.000 nm) | ml/g | 0.135 | 0.095 | 0.074 | 0.046 |
| % Macro Pore Vol. on Tot. P.V. | | 30 | 23 | 22 | 19 |
| MPS [2] | | 780 | 281 | 1050 | 480 |

TABLE 2-continued

Catalyst morphological properties

| Catalyst | | Ex. 1 | Ex. 2 | Comp. Ex. 1 | Comp. Ex. 2 |
|---|---|---|---|---|---|
| Apparent Density | g/ml | 0.59 | 0.60 | 0.72 | 0.86 |
| Bed Void Fraction [3] | | 0.54 | 0.56 | 0.54 | 0.52 |

[1] Total Pore Volume = 1/(Particle Density) − (True Density).
[2] Pore Diameter at the maximum of the Macro Pore Volume Distribution Curve.
[3] Bed Void Fraction = 1 − Apparent Bulk Density/Particle Density.

TABLE 3

Catalyst Performance (coolant temperature = 210° C.; pressure = 0.5 bar)

| | Catalyst | | Ex. 1 | Ex. 2 | Comp. Ex. 1 | Comp. Ex. 2 |
|---|---|---|---|---|---|---|
| Cat. bed | Height | cm | 80 | 80 | 80 | 80 |
| | Volume | ml | 420 | 420 | 420 | 420 |
| Cat. loading | | g | 246.58 | 251.2 | 303.85 | 360.56 |
| Cat. Bulk density | | g/ml | 0.59 | 0.60 | 0.72 | 0.86 |
| Feed | Tot. feed | Nl/h (*) | 771.7 | 756.0 | 761.3 | 772.9 |
| | HCl | Nl/h | 73.3 | 72.9 | 70.3 | 73.5 |
| Feed molar ratio | | HCl/$C_2H_4$ | 0.32 | 0.31 | 0.30 | 0.31 |
| | | $O_2/C_2H_4$ | 0.09 | 0.09 | 0.09 | 0.09 |
| Termal | T10 cm | ° C. | 288 | 247 | 269 | 304 |
| profile | T20 cm | ° C. | 315 | 306 | 287 | 317 |
| cat. bed | T30 cm | ° C. | 292 | 303 | 272 | 283 |
| | T70 cm | ° C. | 220 | 221 | 220 | 218 |
| Conversion | HCl | % mol | 98.66 | 99.18 | 99.0 | 96.4 |
| $C_2H_4$ | mol. select. | CO % | 1.34 | 1.09 | 1.18 | 1.97 |
| | | $CO_2$ % | 1.54 | 1.17 | 1.46 | 1.68 |
| | | pure EDC % | 96.73 | 97.29 | 96.96 | 95.93 |
| Specific Productivity $C_2H_4$ to EDC refer cat. bed. Vol. | | gEDC/ml cat · h | 0.38 | 0.38 | 0.37 | 0.37 |
| Specific Productivity refer cat. weight | | gEDC/g cat · h | 0.65 | 0.64 | 0.51 | 0.43 |

(*) Total feed: $C_2H_4$ = 30.4 vol. %, $O_2$ = 2.7 vol. %
HCl = 9.5 vol. %, $N_2$ = 57.4 vol. %.

The disclosures in European Patent Application No. 08172829 from which this application claims priority are incorporated herein by reference.

What is claimed is:

1. Hollow catalyst granules for the oxychlorination of ethylene to 1,2-dichloroethane, said hollow catalyst granules comprising copper chlorides supported on alumina granules and having a total pore volume of 0.4 to 0.55 ml/g, wherein micropores having a diameter less than 7 nm contribute 18-20% of the total pore volume, mesopores having a diameter of 8 to 50 nm contribute 48-58% of the total pore volume, and macropores having a diameter of 50 to 10,000 nm contribute 23-30% of the total pore volume.

2. Hollow catalyst granules according to claim 1, comprising potassium chloride in amount expressed as metal of 0.5-3 wt % and optionally one or more chlorides of the metals selected from the group consisting of the alkali metals different from potassium, the alkaline earth metals and the rare earth metals in amount of 0.5-3 wt % as alkali metal, 0.05-2 wt % as alkaline earth metal and 0.1-3 wt % as rare earth metals.

3. Hollow catalyst granules according to claim 1, wherein the average pore diameter is from 12 to 20 nm.

4. Hollow catalyst granules according to claim 1, wherein the total pore volume is 0.40-0.48 ml/g.

5. Hollow catalyst granules according to claim 2, wherein copper is in an amount of 4 to 10 wt % and wherein the alkali metal is potassium and/or cesium, the alkaline earth metal is magnesium, and the rare earth metal is cerium.

6. Hollow catalyst granules according to claim 5, wherein the amount of potassium and/or cesium is 0.5-3 wt %, the amount of magnesium is 0.1-2 wt %, and the amount of cerium is 0.5-2 wt %.

7. Hollow catalyst granules according to claim 1, wherein the granules have a hollow cylinder shape with an external diameter of 4-6 mm, internal diameter of 1-3 mm, and height of 4-7 mm.

8. Hollow catalyst granules according to claim 1, having a trilobed cylindrical cross-section, wherein each lobe has a through bore parallel to the axis of the granule and equidistant from axes of other lobes.

9. Hollow cylindrical granules of gamma alumina having a total pore volume of 0.55 to 0.75 ml/g, wherein micropores having a diameter less than 7 nm contribute 15-26% of the total pore volume, mesopores having a diameter of 8 to 50 nm contribute 38-57% of the total pore volume, and macropores having a diameter of 50 to 10,000 nm contribute 17-22% of the total pore volume.

10. Hollow cylindrical granules according to claim 9, provided with one or more through bores parallel to the axis of the granule.

11. Hollow cylindrical granules according to claim 9, wherein the granules are cylinders having an external diameter of 4 to 6 mm, internal diameter of 1 to 3 mm, and height of 4 to 7 mm.

12. A process for the oxychlorination of ethylene to 1.2 dichloroethylene comprising performing the oxychlorination in fixed bed comprising the catalyst granules of claim 1 using air or oxygen as oxidizer at temperatures from 200° to 300° C. with molar ratios $HCl/C_2H_4/O_2$ of 1:1.99:0.51 when using air and of 1:0.70:1.79 when using oxygen.

13. The process of claim 12 carried out using oxygen as oxidizer and three reactors in series, wherein the third reactor is loaded with a fixed bed formed or comprising the catalyst granules according to claim 1, and wherein the molar ratios $HCl/C_2H_4$, $O_2/C_2H_4$ and $HCl/O_2$ are respectively of 0.15 to 0.50, 0.04 to 0.10 and 3.20 to 5.8.

\* \* \* \* \*